United States Patent
Mahon et al.

(10) Patent No.: US 7,180,606 B2
(45) Date of Patent: Feb. 20, 2007

(54) MACHINE VISION SYSTEM FOR MEASURING HEIGHTS OF ITEMS

(75) Inventors: James Mahon, Dublin (IE); Padraig Butler, County Westmeath (IE); John Milroy, County Mayo (IE); Kevin Godden, Dublin (IE); Mohsen Abdollahi, Huntsville, AL (US); Peter Conlon, County Dublin (IE)

(73) Assignee: MV Research Limited, Dublin (IE)

( * ) Notice: Subject to any disclaimer, the term of this patent is extended or adjusted under 35 U.S.C. 154(b) by 61 days.

(21) Appl. No.: 10/885,315

(22) Filed: Jul. 7, 2004

(65) Prior Publication Data

US 2004/0239950 A1 Dec. 2, 2004

Related U.S. Application Data

(63) Continuation of application No. PCT/IE03/00004, filed on Jan. 20, 2003.

(60) Provisional application No. 60/349,238, filed on Jan. 18, 2002, provisional application No. 60/349,242, filed on Jan. 18, 2002.

(51) Int. Cl.
*G01B 11/24* (2006.01)

(52) U.S. Cl. .................... 356/607; 356/622; 356/237.1

(58) Field of Classification Search .. 356/237.1–237.5, 356/601–624, 394
See application file for complete search history.

(56) References Cited

U.S. PATENT DOCUMENTS

| | | | |
|---|---|---|---|
| 4,105,925 A * | 8/1978 | Rossol et al. .......... | 250/559.37 |
| 4,650,333 A * | 3/1987 | Crabb et al. ................ | 356/606 |
| 4,705,401 A * | 11/1987 | Addleman et al. .......... | 356/606 |
| 5,102,224 A * | 4/1992 | Uesugi et al. .............. | 356/607 |
| 5,105,149 A | 4/1992 | Tokura ....................... | 324/158 |
| 5,621,814 A * | 4/1997 | Honda ........................ | 382/152 |
| 5,780,866 A | 7/1998 | Yamamura et al. ........ | 250/559 |
| 5,835,241 A * | 11/1998 | Saund ......................... | 358/488 |
| 6,052,189 A * | 4/2000 | Fuse et al. .................. | 356/615 |
| 6,084,663 A | 7/2000 | Seng .......................... | 356/237 |
| 6,222,630 B1 * | 4/2001 | Wasserman ................ | 356/388 |
| 6,496,270 B1 * | 12/2002 | Kelley et al. ............... | 356/602 |
| 6,654,115 B2 * | 11/2003 | Zemer et al. ............. | 356/237.5 |
| 6,678,062 B2 * | 1/2004 | Haugen et al. ............. | 356/623 |
| 2005/0162644 A1 * | 7/2005 | Watanabe ................ | 356/237.1 |

FOREIGN PATENT DOCUMENTS

| | | |
|---|---|---|
| EP | 0452905 | 10/1991 |
| EP | 0563829 | 10/1993 |
| EP | 0935135 | 8/1999 |
| JP | 02002098513 A * | 4/2002 |

* cited by examiner

*Primary Examiner*—Hoa Q. Pham
(74) *Attorney, Agent, or Firm*—Jacobson Holman PLLC

(57) ABSTRACT

A machine vision system (1) has two laser sources (2, 3) to illuminate a solder deposit from both sides for comprehensive coverage without occlusion. The camera (4) has an FGPA (32) programmed to define a subset of the sensor array (20) as a region of interest to be processed for each laser source (2, 3). This reduces the amount of data transfer and processing required. The image line (31) is dynamically maintained in the region of interest by adjustement of camara Z position according to warp of the substrate (S).

12 Claims, 5 Drawing Sheets

MACHINE VISION SYSTEM FOR MEASURING HEIGHTS OF ITEMS

This is a continuation of PCT/IE03/00004 filed Jan. 20, 2003 and published in English which in turn is based on provisional Application No. 60/349,238 filed Jan. 18, 2002 and provisional Application No. 60/349,242 filed Jan. 18, 2002.

FIELD OF THE INVENTION

The invention relates to a machine vision system for measurement of height of items such as solder deposits on a substrate with measurement in X, Y, and Z dimensions.

PRIOR ART DISCUSSION

Our prior European Patent Application No. EP0935135 describes such a system. A laser beam is directed at an angle to the scene so that it reflects as a line the shape of which indicates the height at the scene. This system also includes additional high-level and low-level LED illumination. The undulating pattern and peaks of the reflected laser line indicate primarily Z dimension of the solder deposits and some XY information is also gleaned from this line. The LED illumination provides additional XY information.

There is an ever-present requirement to increase speed of operation of such systems to cope with increasing product throughputs. At the same time there is a desire to improve measurement accuracy.

SUMMARY OF THE INVENTION

According to the invention, there is provided a machine vision system comprising a light source for generating a structured line of illumination and directing it at an angle to normal to a scene having a substrate and items deposited on the substrate, a camera having a sensor array for capturing an image line, and an image processor for determining scene height data according to pattern of the image line, characterised in that, the camera processes only a subset of sensor array pixels, in a pre-defined region of interest;
the system further comprises means for determining extent of warp in the substrate; and
the system further comprises means for compensating for warp of the substrate to dynamically maintain the image line within the region of interest.

In one embodiment, the compensation means comprises a motion controller for dynamically adjusting distance between the camera and the substrate.

In another embodiment, the means for determining extent of warp comprises a function in the image processor for determining warp in response to shifting of the image line with respect to boundaries of the region of interest.

In a further embodiment, the image processor is operable to capture images line for a plurality of scan passes across the substrate, to generate warp data in each scan, and to use said warp data to dynamically control camera-to-substrate distance in a next scan.

In one embodiment, the image processor is operable to generate warp data for a pre-profile scan across the substrate, and for using said warp data for dynamic adjustment in a first scan across the substrate.

In another embodiment, the image processor is operable to acquire anchor image data for a scan between two mutually remote spaced-apart areas of the substrate between which there are no items to provide warp data for a first scan in a spaced-apart area of the substrate.

In a further embodiment, the motion controller is operable to dynamically adjust camera position according to substrate warp.

In one embodiment, the motion controller is operable to adjust camera position to a resolution of at least 0.25 microns.

In another embodiment, a firmware circuit connected to the sensor array is operable to control the region of interest in response to received instructions.

In a further embodiment, the system comprises at least two line light sources each directing a line of light in different directions at an item to ensure comprehensive scene coverage without occlusion.

In one embodiment, there is sensor array region of interest associated with each light source.

According to another aspect, the invention provides a method of operation of a machine vision system for analysing height of items deposited on a substrate, in which a line of light is directed at an item at an angle to normal to the substrate, and pattern of an image line detected by a camera indicates height of the item, wherein the camera processes only a subset of sensor array pixels in a pre-defined region of interest; the system dynamically determines warp of the substrate, and the system dynamically compensates for the warp to dynamically maintain the image line within the region of interest.

In one embodiment, the system determines warp of the substrate by monitoring shifting of the image line with respect to boundaries of the region of interest.

In another embodiment, the camera captures an image line in each of a plurality of scans across the substrate, the image processor generates warp data in each scan, and the system dynamically compensates for warp in the next scan according to said warp data.

In a further embodiment, two light lines are directed at the scene from different directions to avoid occlusion, and there is a separate region of interest for each line.

In one embodiment, the system dynamically compensates for warp by adjusting distance between the camera and the substrate.

DETAILED DESCRIPTION OF THE INVENTION

Brief Description of the Drawings

The invention will be more clearly understood from the following description of some embodiments thereof, given by way of example only with reference to the accompanying drawings in which.

DESCRIPTION OF THE EMBODIMENTS

Figure 1:
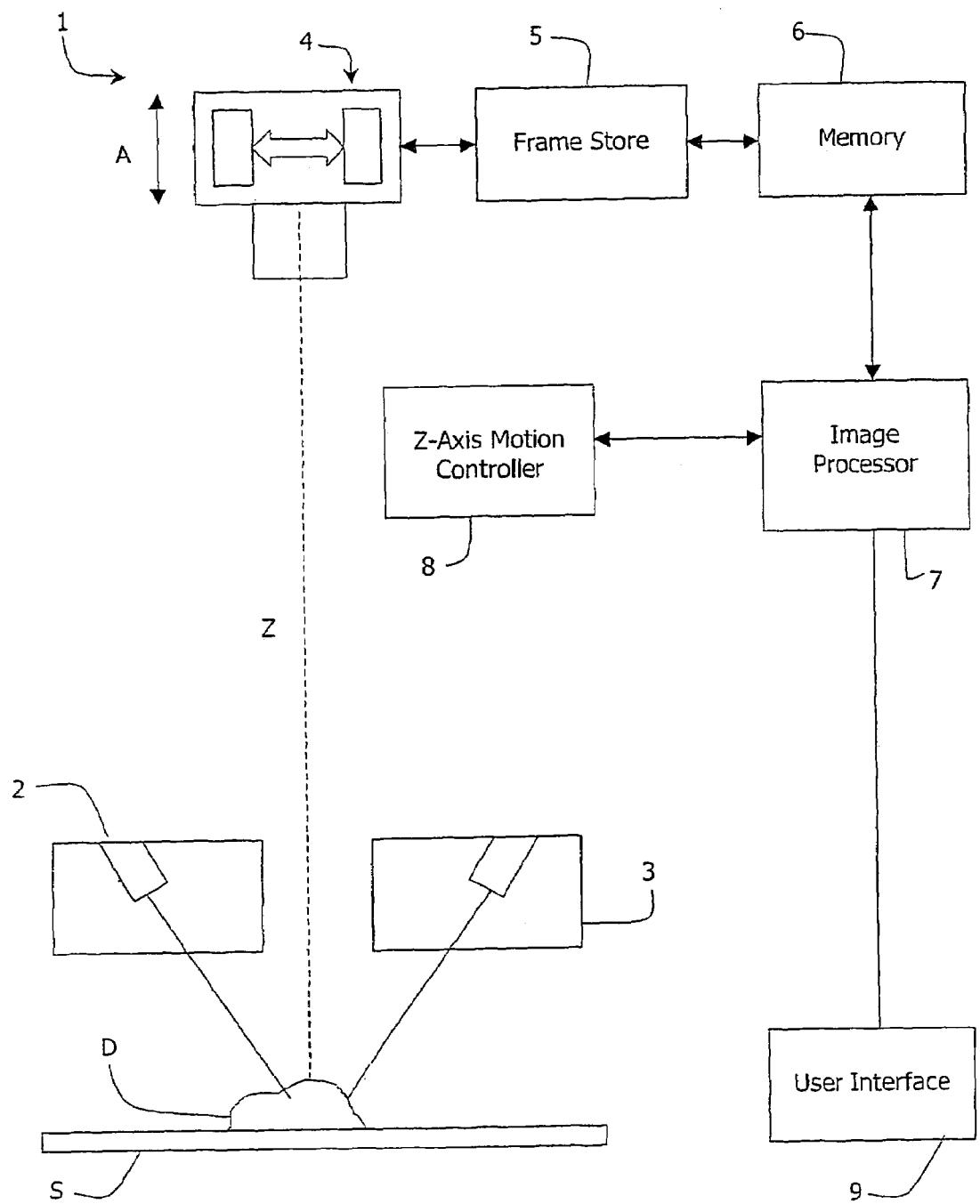
FIG. 1 is a block diagram illustrating a machine vision system of the invention.

Referring to FIG. 1 a machine vision system 1 is used for analysing solder deposits D on a substrate S. The system 1 has a host processor, not shown, for overall control. The system 1 comprises two opposed laser line sources 2 and 3, each mounted at an angle to normal to the substrate S so that height data can be gleaned from a pattern of the image line captured by a normal (Z-axis) CMOS camera 4.

The CMOS camera 4 is mounted directly over the scene in the Z direction. It is connected to a frame store ("framegrabber") 5, in turn connected to a random access memory (RAM) 6. An image processor 7 of hardware and software processes the image data in the RAM 6 and generates motion feedback for a camera motion controller 8 and outputs to a user interface 9 for a process engineer. In FIG. 1, the laser sources 2 and 3 are shown mounted at similar angles to the plane of the substrate S. However, in other embodiments they are at different angles to this plane in order to capture additional information, as described in more detail below.

Figure 2:
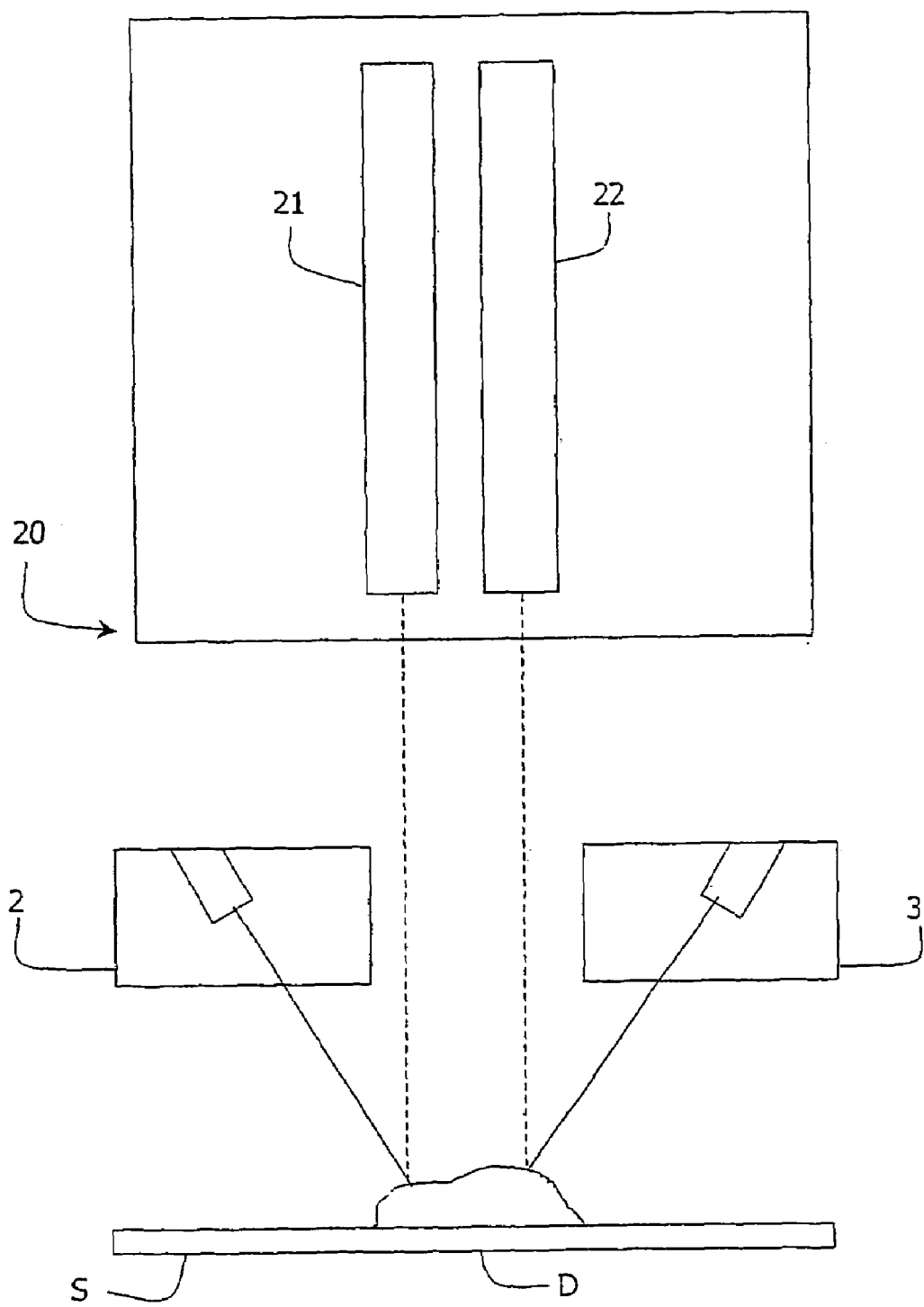
FIG. 2 is a diagrammatic representation showing capture of images for illumination from opposed directions.

The camera 4 is programmed to process one or more particular regions of interest ("ROI") in a full array 20 of CMOS pixels in the camera 4. Referring to FIG. 2, there are two ROIs 21 and 22 in the CMOS array 20, one for each of the laser sources 2 and 3 respectively.

Figure 3:
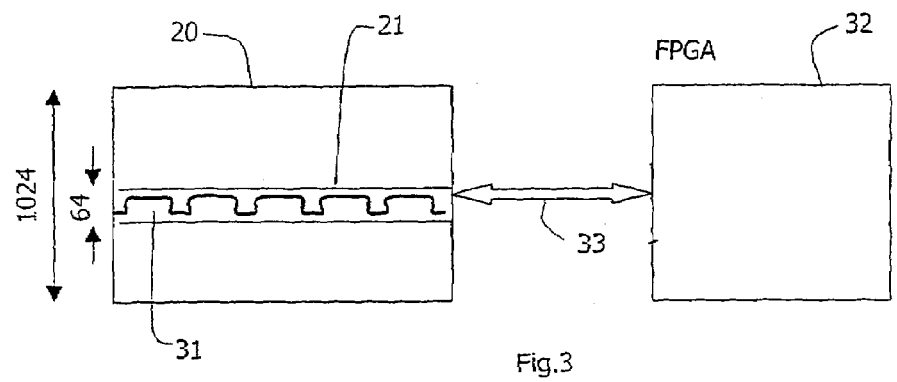
FIG. 3 is a diagram showing internal camera operation.

Referring to FIG. 3 the camera 4 comprises the CMOS array 20 connected to a field programmable gate array (FPGA) 32. The FPGA 32 captures the basic image data from the array 20 on an interface 33. This interface has a limited bandwidth, and in prior art machine vision systems it often limits overall processing speed. However, in this embodiment this problem is overcome by virtue of the need to transfer only the data for the particular ROIs. The sensor 20 has a maximum data transfer rate which is fixed. Reducing the ROI size allows the frame rate to be increased while keeping within the maximum data transfer rate. For example, if each ROI size is 50 pixel lines×1280 and the interface 33 bandwidth is 660 MHz, then the sensor array 20 can output 10 k frames (ROIs) per second (660 MHz/(50× 1280)). Higher resolution of dynamic Z adjustment allows the ROI sizes to be reduced, further increasing the frame rate and hence the overall speed of operation.

The FPGA 32 performs low-level processing including control of image capture, set-up and maintenance of the ROI's, providing an interface to the framestore 5, and generating range data from the ROI image data. The FPGA 32 implements an algorithm to provide a single 8-bit output per frame (ROI).

Figure 4A:
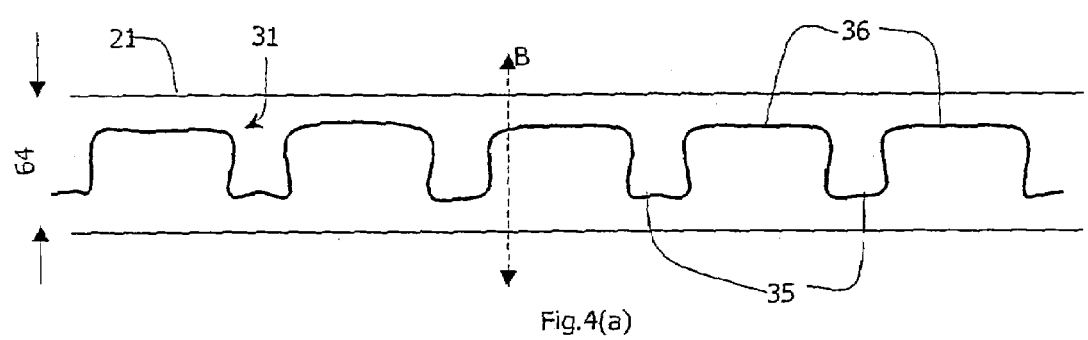
FIGS. 4(a) and 4(b) are representations of image lines in a region of interest.
Figure 4B:
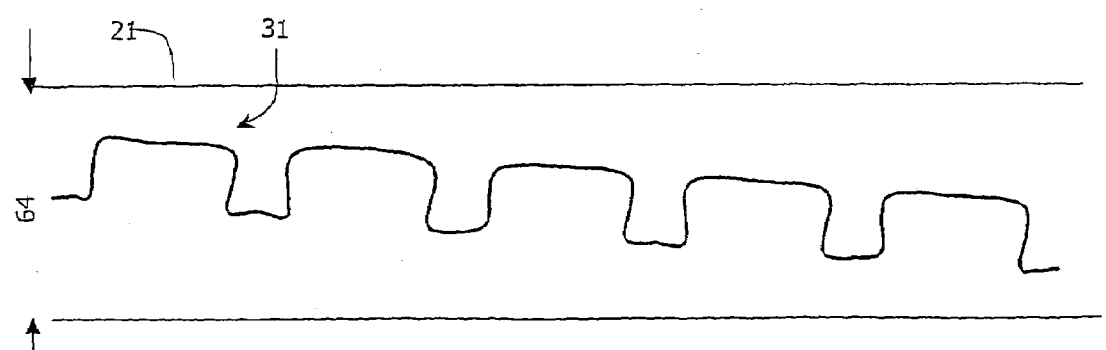

As shown in FIG. 4(a), a line 31 reflected from the scene has an irregular undulating pattern corresponding to the pattern of a row of the deposits D on the substrate S illuminated by one of the laser sources 2 or 3. The general nature of this image line is described in our prior European Patent Specification No. EP0935135. For clarity, only one of the image lines and associated ROI is illustrated. Referring particularly to FIG. 4(a) the bottom parts 35 of the image line 31 correspond to the substrate and the top portions 36 correspond to the tops of the paste deposits. It will be appreciated that the image line 31 is well within the ROI 21, even though the ROI has a width of only 64 pixel lines or less out of the total of 1024 pixel lines in the array 20. The arrowed lines B in FIG. 4(a) show the direction of offset of the image line 31 with warp of the substrate S causing a uniform translational shift along the scan line. Of course, there may be warp in the normal direction to this i.e. the Z axis value changes along the length of the row of deposits D. Such warp tends to skew the image line 31 as shown in FIG. 4(b). Alternatively, the warp may have components from both directions.

In this embodiment, the prior art limitation imposed by bandwidth of the interface 33 has effectively been eliminated by programming the FPGA 32 (typically at start-up) with the ROI 21. Each line of the sensor array 20 is individually addressable. The array 20 is setup to start outputting image data starting at a particular line and ending at another line, thus defining an ROI 21. Thus only pixels from 64 pixel lines or less are passed for each laser line ROI, in this case two. This is much less than the full number, 1024. The FPGA 32 implements the ROI definitions in the array 20 upon receipt of an instruction (typically at set-up) from the processor 7. However, a potential problem with this approach is that substrate warp can bring the image line 31 out of the ROI, thus causing the system to miss valuable data. This problem is avoided by the image processor 7 dynamically monitoring position of the image line 31 for either translational offset in a direction B or skewing as shown in FIG. 4(b). In response to detection of warp, the processor 7 generates a motion control signal for the controller 8, causing it to dynamically adjust the Z position height) of the camera 4. A primary goal of the dynamic Z adjustment provided by monitoring the reflected laser line 31 within the ROI 21 is that the position of the line will always remain at or as close to some fixed nominal position. Typically this nominal position is set such that the image line is at or a few pixels (<10) above the bottom of the ROI. Doing so allows the system to use the smallest possible frames to give the highest frame rate. Tight control of Z position provides accurate tracking of the substrate warp, thus allowing the system to reduce the size of the ROI 21. A reduced ROI 21 size means increased frame rate which in turn means faster inspection times.

Z-axis adjustment is most effective at compensating for "offset" warp. Since the Z moves along a single axis and since the image sensor is a 2D device "skew" warp cannot be fully compensated for. The system maintains as much of the "skew" line as possible within the ROI. If the substrate itself has no warp but its position is offset in Z from an expected level then this situation can be compensated at the start of the inspection. However "offset" warp compensation occurs during the individual scans that make up an entire inspection. The controller 8 can adjust the camera 4 position to a resolution determined by the resolution of the motor used to position the Z-axis—this is, the minimum step size. In this embodiment this is 0.25 microns. Such a resolution may not be required for all applications. For example if the system were used to measure taller objects then the minimum step size could be increased. In all cases the resolution is adequate to dynamically maintain the image lines within the relevant ROIs even with substrate warp. This adjustment dynamically maintains the image line 31 centrally within its ROI for optimum image acquisition, effectively cancelling out substrate warp on-the-fly.

Dynamic adjustment may alternatively be controlled by the FPGA or other circuit within the camera if it is important to reduce latency in the feedback loop to the motion controller 8. Also, the Z-axis adjustment may alternatively or additionally move the position of the substrate S.

As is clear from FIG. 2, the use of two opposed laser sources provides full "view" of the deposit D. Because there are two image lines for at least some of the deposits D, the processor 7 acquires much more useful information to process. It avoids occlusion and shadowing, i.e. the inability to "see" that part of the deposit which is occluded from view. The additional image processing required is more than compensated for by the use of ROIs.

Figure 5:
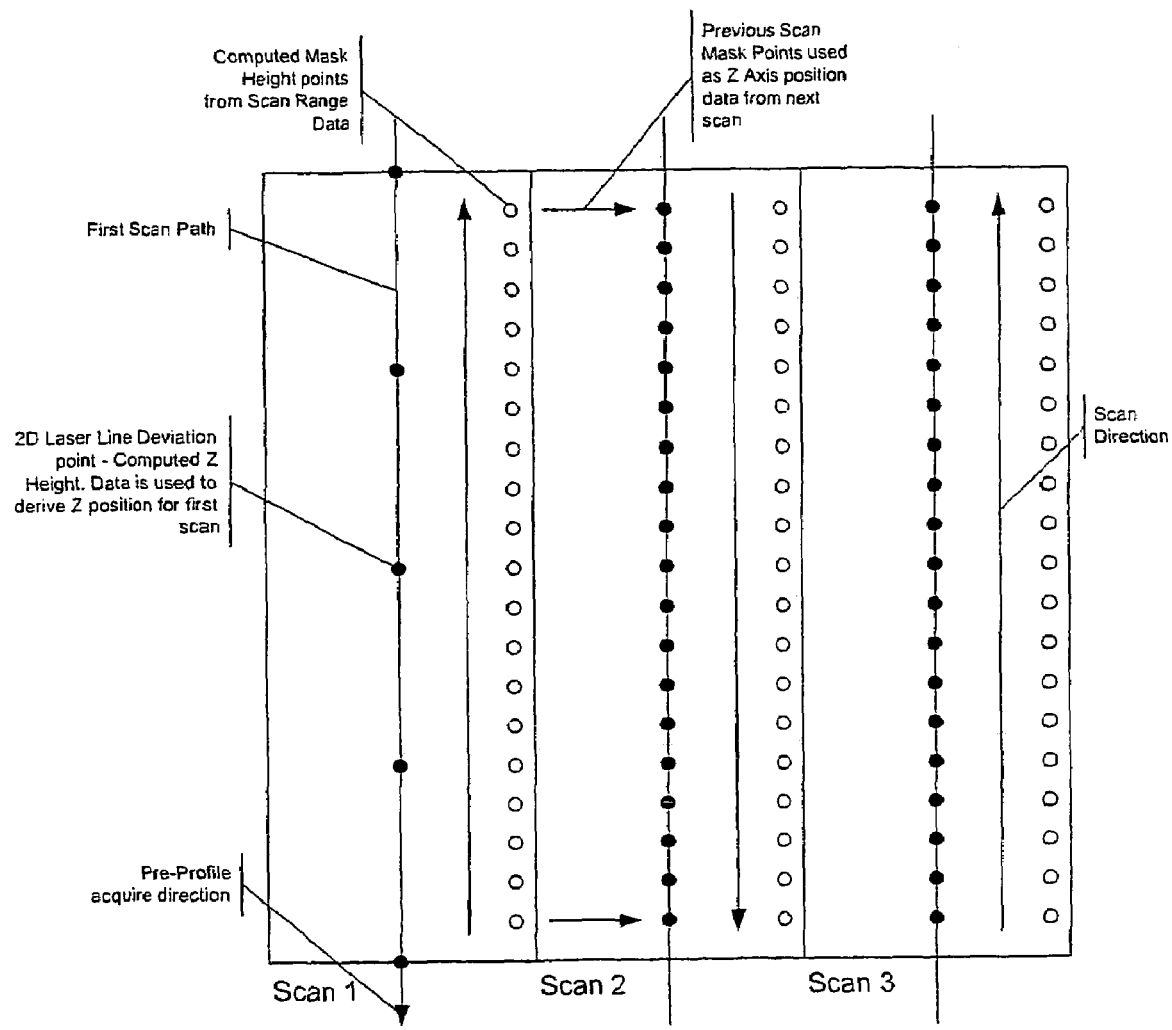
FIG. 5 is a diagram showing a scanning pattern.

FIG. 5 shows how dynamic Z camera positioning operates, in a number of simple steps:

Pre-Profile Step 1:

Acquire a series of 2D images with one laser enabled. This is along a line of the board without any solder deposits. The inspection sequence is a) locate and inspect fiducials, b) acquire the anchor points along a pre-profile scan path and c) perform scans—chaining XY table moves together so as to minimise total move distance. The pre-profile line along which the anchor points are acquired is CAD dependant. After the system has located the last fiducial it will generate the inspection plan which determines how the scans will be executed. The start of the inspection plan will be as near to the position of the last fiducial as possible, minimising the XY table moves. The anchor points will be gathered along the path of the first scan of the inspection. For each image the deviation of the laser line in the image is directly proportional to the board warp at that point. These board warp points (anchor points) are then used to define the Z positions during the first scan.

Scanning Step 2:

Perform the first scan using the board warp profile acquired during Step 1. The scan profile is represented as data derived from the scan grey scale information where each grey scale value corresponds to an actual height (~5 μm per grey scale set by calibration). Dynamic Align points are gathered every 1000 pixel lines (where each pixel line corresponds to 20 μm) and three points across the scan width, left, centre and right.

In each scan (pre-profile and also subsequent) Dynamic Align Z data is gathered to indicate board warp. This data is used in the next scan. The pre-profile scan provides this data for the first scan. For the subsequent scans even though the solder deposits will vary in height and so there will be non-uniformity in the image lines, warp is still determined according to the start positions of the line for each deposit D. The dynamic data gathered from the scan data is derived from an average height at that dynamic data point. If the system were to use the instantaneous height data provided by a single line then the Z-axis movement would be noisy. The anchor points provide a reference points gathered by the system. The data gathered during each scan is relative data, relative to the reference point determined at the start of the first scan.

The processor 7 needs to know if the inspection takes place from Left To Right (default) or from Right To Left, as would be the case if the plan was reversed. This determines whether the left or right height points are used to predict the position of Z in the next scan. So if the inspection direction is Left to Right then Right points will be used.

Step 3:

Repeat step 2 for each subsequent scan.

The following assumptions are made in programming the processor 7:

All scans are the same length (i.e. the length of the longest scan). Though this need not be the case, making scans the same length allows for easy implantation of the Dynamic Z algorithm.

The deviation from the edge of scan N to the centre of scan N+1 is negligible.

The entire board is covered, with no scan gaps.

Figure 6:
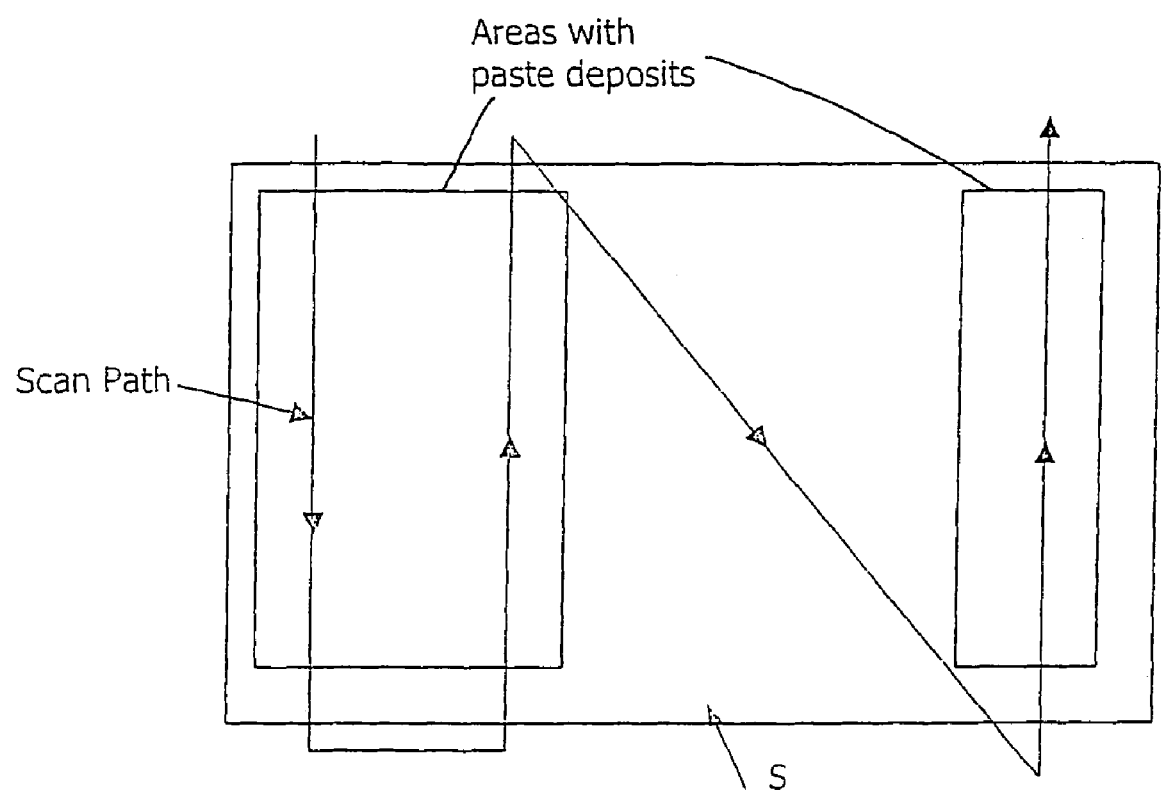
FIG. 6 is a diagram showing a scanning pattern for a substrate with deposit areas spaced-apart.

However, in some situations the final assumption above can not be made. Such a situation is illustrated in FIG. 6. In this scenario only a part of the board on the left side as viewed in FIG. 6 has many deposits, another region being spaced-apart to the right. In this scenario, the last scan in the left hand region is too far away from the first scan of the right-hand region. This problem is addressed by adding extra anchor points into the acquisition plan. In this example, anchor points may be added into the middle of the plan between the two regions to provide profile data to remote scans. A remote scan could be classified as a scan which is more than a scan width away from the previous scan.

It will be appreciated that the invention achieves a major increase in frame rate and hence in scan speed with use of conventional hardware components. There is also a considerable improvement in accuracy arising from the embodiments with two laser lines.

The invention is not limited to the embodiments described but may be varied in construction and detail. For example, the laser sources may be mounted at different angles to the substrate plane. In this embodiment, one of the sources may be mounted at an angle of approximately 80° to the substrate plane and the other at 45°.

This allows the system to have multi-resolution capabilities. For "normal" deposits the system could use the ROI in which the reflection of the 45° laser is visible. For higher deposits (or maybe components) the ROI where the 80° laser reflection is visible could be used. In both instances different height deposits could be measured while maintaining ROI's of the same size. A head geometry implemented in such a way could allow the system to perform paste inspection and measurement and also presence/absence detection for SMT devices.

Also, it is envisaged that the warp may be determined other than by analysis of the image lines. For example, a separate optical sensor may be mounted to monitor the level of the board, or an ultrasonic sensor may be used.

Also, in another alternative the motion controller does not perform Z adjustment, and instead the ROIs are dynamically adjusted by the FPGA (or other controller) for the automatic compensation. This embodiment preferably also provides a mechanism to minimise warp so that the camera does not stray from being in focus to a significant extent and relatively little ROI dynamic adjustment is required.

Furthermore, where there is dynamic Z adjustment this may alternatively be performed by adjustment of position of the substrate instead of the camera.

The invention claimed is:

1. A machine vision system comprising:
    a line light source for generating illumination which is reflected from a substrate having items as an undulating line having a pattern corresponding to a pattern of said items on the substrate, in which bottom parts of the line correspond to the substrate and top parts correspond to top portions of said items on the substrate;
    a camera mounted to capture images of said reflected undulating line to provide image lines, wherein the camera has a full array of pixels, and processes only pixels of one or more particular regions of interest in said full array or pixels;
    an image processor for processing one of said image lines to:
        determine scene height according to pattern of said image line, and
        dynamically determine extent of warp in the substrate also according to said image line by dynamically monitoring position of the image line with respect to the region of interest for translational offset of the image line and for skewing of the image line, and generating a motion control signal according to said monitoring; and a motion controller for dynamically adjusting camera-substrate separation so that the position of the image line remains at or close to a fixed nominal position within the region of interest.

2. The machine vision system as claimed in claim 1, wherein the image processor is operable to capture images line for a plurality of scan passes across the substrate, to generate warp data in each scan, and to use said warp data to dynamically control camera-to-substrate distance in a next scan.

3. The machine vision system as claimed in claim 2, wherein the image processor is operable to generate warp data for a pre-profile scan across the substrate, and for using said warp data for dynamic adjustment in a first scan across the substrate.

4. The machine vision system as claimed in claim 2, wherein the image processor is operable to acquire anchor image data for a scan between two mutually remote spaced-apart areas of the substrate between which there are no items to provide warp data for a first scan in a spaced-apart area of the substrate.

5. The machine vision system as claimed in claim 1, 2, wherein the motion controller is operable to dynamically adjust camera position according to substrate warp.

6. The machine vision system as claimed in claim 5, wherein the motion controller is operable to adjust camera position to a resolution of at least 0.25 microns.

7. The machine vision system as claimed in claim 1, wherein a firmware circuit connected to the sensor array is operable to control the region of interest in response to received instructions.

8. The machine vision system as claimed in claim 1, wherein the system comprises at least two line light sources each directing a line of light in different directions at an item to ensure comprehensive scene coverage without occlusion.

9. The machine vision system as claimed in claim 8, wherein there is sensor array region of interest associated with each light source.

10. A method of operation of a machine vision system comprising a line of light source, a camera, an image processor, and a motion controller, the method comprising the steps of:

the line light source generating illumination which is reflected from a substrate having items as an undulating line having a pattern corresponding to a pattern of said items on the substrate, in which bottom parts of the line correspond to the substrate and top parts correspond to top portions of said items on the substrate;

the camera capturing images of said reflected undulating line to provide image lines, wherein the camera has a full array of pixels, and processes only pixels of one or more particular regions of interest in said full array or pixels;

the image processor processing one of said image lines to:
   determine scene height according to pattern of said image line, and
   dynamically determine extent of warp in the substrate also according to said image line by dynamically monitoring position of the image line with respect to the region of interest for translational offset of the image line and for skewing of the image line, and generating a motion control signal according to said monitoring; and the motion controller dynamically adjusting camera-substrate separation so that the position of the image line remains at or close to a fixed nominal position within the region of interest.

11. The method as claimed in claim 10, wherein the camera captures an image line in each of a plurality of scans across the substrate, the image processor generates warp data in each scan, and the system dynamically compensates for warp in the next scan according to said warp data.

12. The method as claimed in claim 10, wherein two light lines are directed at the scene from different directions to avoid occlusion, and there is a separate region of interest for each line.

* * * * *